United States Patent
Eddaoudi et al.

(10) Patent No.: US 10,391,439 B2
(45) Date of Patent: Aug. 27, 2019

(54) TRACE AND LOW CONCENTRATION $CO_2$ REMOVAL METHODS AND APPARATUS UTILIZING METAL ORGANIC FRAMEWORKS

(71) Applicant: King Abdullah University of Science and Technology, Thuwal (SA)

(72) Inventors: Mohamed Eddaoudi, Thuwal (SA); Youssef Belmabkhout, Thuwal (SA); Osama Shekhah, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 173 days.

(21) Appl. No.: 15/507,411

(22) PCT Filed: Sep. 2, 2015

(86) PCT No.: PCT/US2015/048081
§ 371 (c)(1),
(2) Date: Feb. 28, 2017

(87) PCT Pub. No.: WO2016/036814
PCT Pub. Date: Mar. 10, 2016

(65) Prior Publication Data
US 2017/0246584 A1    Aug. 31, 2017

Related U.S. Application Data

(60) Provisional application No. 62/044,928, filed on Sep. 2, 2014, provisional application No. 62/044,927, filed on Sep. 2, 2014.

(51) Int. Cl.
*B01D 53/62*    (2006.01)
*B01D 53/02*    (2006.01)
(Continued)

(52) U.S. Cl.
CPC ............ *B01D 53/02* (2013.01); *A61M 16/22* (2013.01); *B01J 20/226* (2013.01);
(Continued)

(58) Field of Classification Search
None
See application file for complete search history.

(56) References Cited

U.S. PATENT DOCUMENTS

2009/0301493 A1    12/2009    McKenna et al.

OTHER PUBLICATIONS

Nugent et al., "Porous materials with optimal adsorption thermodynamics and kinetics for CO2 separation." Nature, vol. 495, pp. 80-84 (published online on Feb. 27, 2013).*
(Continued)

*Primary Examiner* — Daniel Berns
(74) *Attorney, Agent, or Firm* — Billion & Armitage; Benjamin C. Armitage

(57) ABSTRACT

In general, this disclosure describes techniques for removing trace and low concentration $CO_2$ from fluids using SIFSIX-n-M MOFs, wherein n is at least two and M is a metal. In some embodiments, the metal is zinc or copper. Embodiments include devices comprising SIFSIX-n-M MOFs for removing $CO_2$ from fluids. In particular, embodiments relate to devices and methods utilizing SIFSIX-n-M MOFs for removing $CO_2$ from fluids, wherein $CO_2$ concentration is trace. Methods utilizing SIFSIX-n-M MOFs for removing $CO_2$ from fluids can occur in confined spaces. SIFSIX-n-M MOFs can comprise bidentate organic ligands. In a specific embodiment, SIFSIX-n-M MOFs comprise pyrazine or dipryidilacetylene ligands.

20 Claims, 6 Drawing Sheets

(51) Int. Cl.
*B01D 53/80* (2006.01)
*B01D 53/81* (2006.01)
*B01D 53/96* (2006.01)
*B01J 20/22* (2006.01)
*B01J 31/16* (2006.01)
*A61M 16/22* (2006.01)
*B01J 20/28* (2006.01)
*H01M 8/0668* (2016.01)

(52) U.S. Cl.
CPC ... *B01J 20/28057* (2013.01); *B01J 20/28083* (2013.01); *H01M 8/0668* (2013.01); *B01D 2253/204* (2013.01); *B01D 2257/504* (2013.01); *B01D 2258/0283* (2013.01); *B01D 2258/06* (2013.01); *B01D 2259/4533* (2013.01); *B01J 2220/62* (2013.01); *Y02C 10/08* (2013.01)

(56) References Cited

OTHER PUBLICATIONS

Supplementary Information for Nugent et al., "Porous materials with optimal adsorption thermodynamics and kinetics for CO2 separation." Nature, vol. 495, pp. 80-84 (published online on Feb. 27, 2013).*

"International Search Report and Written Opinion", International Application No. PCT/US2015/048081, dated Nov. 13, 2015, 11 pages.

Shekhah, et al., "Made-to-order metal=organic frameworks for trace carbon dioxide removal and air capture", Nature Communications, Jun. 25, 2014, 1-7.

Choi, et al., "Application of Amine-Tethered Solid Sorbents for Direct CO2 Capture from the Ambient Air", Environ. Sci. Technol. 2011, 45, 2420-2427.

Choi, et al., "Modification of the Mg/DOBDC MOF with Amines to Enhance CO2 Adsorption from Ultradilute Gases.", J. Phys. Chem. Lett., 2012, 3 (9), pp. 1136-1141.

Didas, et al., "Role of amine structure on carbon dioxide adsorption from ultradilute gas streams such as ambient air", ChemSusChem 2012, 5, 2058-2064.

Goeppert, et al., "Air as the renewable carbon source of the future: an overview of CO2 capture from the atmosphere", Energy Environ. Sci., 2012, 5, 7833-7853.

Major et al., "Carbon dioxide removal from air by adsorbents", Ind. Eng. Chem. Proc. Res. Develop. 4, 327-333, Jul. 1965.

McDonald, et al., "Capture of Carbon Dioxide from Air and Flue Gas in the Alkylamine-Appended Metal-Organic Framework mmen-Mg2(dobpdc)", J. Am. Chem. Soc. 2012, 134, 7056-7065.

Nikulshina, "CO2 capture from atmospheric air via consecutive CaO-carbonation and CaCO3-calcination cycles in a fluidized-bed solar reactor", Chem. Eng. J. 146, 2009, 244-248.

Rege, et al., "Air prepurification by pressure swing adsorption using single/layered beds", Chem. Eng. Sci. 56, 2001, 2745-2759.

Rege, et al., "Sorbents for air prepurification in air separation", Chem. Eng. Sci. 55, 2000, 4827-4838.

Stolaroff, et al., "Carbon dioxide capture from atmospheric air using sodium hydroxide spray", Environ. Sci. Technol. 42, 2728-2735.

* cited by examiner

TRACE AND LOW CONCENTRATION $CO_2$ REMOVAL METHODS AND APPARATUS UTILIZING METAL ORGANIC FRAMEWORKS

BACKGROUND

Direct air capture can mitigate the increasing $CO_2$ emissions associated with the carbon polluting sources. Efficient and cost-effective removal of trace $CO_2$ is important in various key industrial applications pertaining to energy, environment and health. From an industry prospective, the removal of trace $CO_2$ from air is a growing area of research and development due to its substantial importance for pre-purification of air and particularly when atmospheric air is used during the separation of nitrogen and oxygen.

The amount of $CO_2$ in the atmosphere continues to rise rather rapidly due to unparalleled cumulative $CO_2$ emissions, provoking the undesirable greenhouse gas effect. Certainly, it is becoming critical to develop economical and practical pathways to reduce $CO_2$ emissions. Appropriately prospective routes to address this enduring challenge have been considered: (i) $CO_2$ emission reduction from post-combustion stationary and mobile sources where $CO_2$ concentration is in the range of 10-15% and (ii) $CO_2$ removal from air, called direct air capture (DAC), which is another alternative option to reduce greenhouse gases emissions in a uniform way globally. Although DAC is relatively more challenging than post-combustion capture, it is recognized that it might be practical, provided that suitable adsorbent combining optimum uptake, kinetics, energetics and $CO_2$ selectivity is available at trace $CO_2$ concentrations.

In an example, prior to air separation using cryogenic distillation or pressure swing adsorption (PSA), air must be $CO_2$ free to avoid (i) blockage of heat-exchange equipment as a result of frozen $CO_2$ during the liquefaction process and (ii) adsorbents (e.g., zeolites) contamination used for oxygen production by pressure swing adsorption (PSA).

Equally important, alkaline fuel cells (AFCs) require a $CO_2$ free feedstock of oxygen and hydrogen gases as it is widely recognized that trace amounts of $CO_2$ (i.e. 300 ppm) degrade the electrolyte in AFCs. Furthermore, efficient removal of $CO_2$ at low concentrations is also vital for the proper operation of breathing systems in confined spaces such as submarines and aerospace shuttles.

Efficient $CO_2$ removal and resupply of fresh air is also critical in mining and rescue missions, diving, and most importantly in medical applications such as anaesthesia machines. The use of anaesthesia machine is still a growing clinical trend worldwide, driven by the need to reduce cost and improve patient care via the use of efficient $CO_2$ sorbents. A $CO_2$ removal feature in anaesthesia machine is particularly important in semi-closed or closed rebreathing systems, as the rebreathing fraction is at least 50% of the exhaled gas volume, directed back to the patient after proper $CO_2$ removal in the next exhalation. Currently, common sorbents for this application are non-recyclable, and generate large amounts of unwanted medical waste.

There is a pressing need to develop novel porous materials that can adequately address the growing interest to low $CO_2$ concentration removal applications. Only a few materials were reported to adsorb efficiently traces of $CO_2$, particularly with regards to DAC using a variety of amine supported materials (e.g. porous silica). However, these materials contain primary amines which require high energy for regeneration, such as about 80-120 kJ/mol, in part due to the materials' chemical adsorption mechanisms. Additionally, amine grafting is conducted in a step separate from the platform material synthesis, thus adding additional cost and time to manufacturing.

Modular and tunable porous materials, namely metal-organic frameworks (MOFs), can be used to tackle this ongoing challenge. Recently, MOFs were intensively investigated for intermediate and high $CO_2$ concentration removal applications such as post-combustion, pre-combustion capture, natural gas and biogas upgrading. Nevertheless, the potential of MOFs to remove traces and low $CO_2$ concentration from gas streams was rarely considered. The main reason for this lack of studies is that most MOFs reported so far, with or without unsaturated metal sites (UMC) or/and functionalized ligands, exhibit relatively low $CO_2$ selectivity and uptake particularly at relatively low $CO_2$ partial pressure. To overcome this downfall, various research groups have adopted the amine grafting chemistry and the acquired knowledge from amine-supported silica, as a prospective pathway to enhance the $CO_2$ adsorption energetics and uptake in MOFs and covalent organic frameworks (COFs). Markedly, the few reported strategies targeting air capture using MOFs are centred on the aptitude of grafted amines to form a strong chemical bond (at least 70 $kJ \cdot mol^{-1}$) with $CO_2$, affording high affinity toward $CO_2$ and therefore high $CO_2$ selectivity. Particularly, ethylenediamine (ED) grafting on Mg-MOF-74 supports have been studied for $CO_2$ adsorption from ultra-dilute gas streams such as ambient air. Similarly, N,N-dimethylethylenediamine grafting for DAC using an expanded isostructure of Mg-MOF-74 has also been studied. All such materials suffer from the drawbacks of amine grafted materials as discussed above.

SUMMARY

In general, this disclosure describes techniques for removing $CO_2$ from fluids using SIFSIX-n-M MOFs, wherein n is at least two and M is a metal. In some embodiments, the metal is zinc or copper. Embodiments include devices comprising SIFSIX-n-M MOFs for removing $CO_2$ from fluids. In particular, embodiments relate to devices and methods utilizing SIFSIX-n-M MOFs for removing $CO_2$ from fluids, wherein $CO_2$ concentration is trace. Methods utilizing SIFSIX-n-M MOFs for removing $CO_2$ from fluids can occur in confined spaces. SIFSIX-n-M MOFs can comprise bidentate organic ligands. In a specific embodiment, SIFSIX-n-M MOFs comprise pyrazine or dipryidilacetylene ligands.

The details of one or more examples are set forth in the accompanying drawings and the description below. Other features, objects, and advantages will be apparent from the description and drawings, and from the claims.

BRIEF DESCRIPTION OF THE DRAWINGS

The accompanying drawings illustrate non-limiting example embodiments of the invention.

DETAILED DESCRIPTION

Figure 1A:
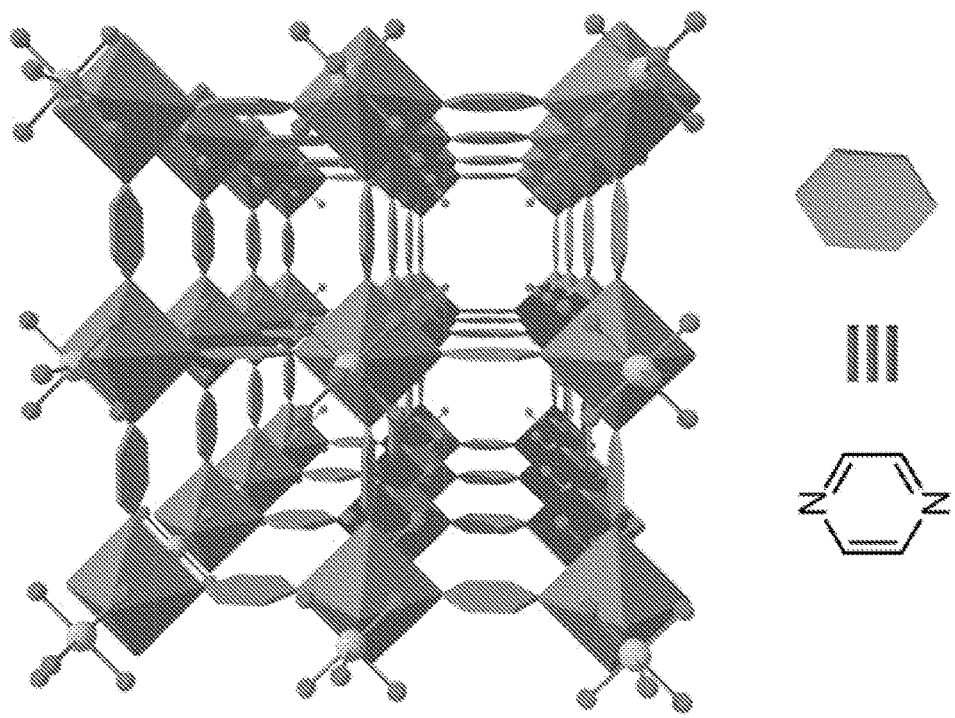
FIG. 1A illustrates a SIFSIX-n-M MOF coordinated by pyrazine ligands, according to one or more embodiments.

The present invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It should be understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The present disclosure provides SIFSIX-n-M MOFs for use in trace and low $CO_2$ concentration removal, and $CO_2$ sequestration in confined spaces. A particular advantage of SIFSIX-n-M MOFs is high $CO_2$ removal efficiency at very low $CO_2$ partial pressure without any post-functionalization (e.g., amine functionalization), thereby eliminating costly and inefficient processing steps as necessary with amine functionalized MOFs. A further advantage is the ability to regenerate and reuse SIFSIX-n-M MOFs after $CO_2$ capture. Generally, energy for regenerating SIFSIX-n-M MOFs as provided herein is only about 45-55 kJ/mol, as compared to 80-120 kJ/mol for amine functionalized materials.

As used herein, "trace" refers to species concentrations which are less than about 10%, less than about 7.5%, less than about 5%, less than about 2.5%, or less than about 1% of a system. "Trace" can additionally or alternatively refer to a species having a partial pressure below about 125 mbar, below about 100 mbar, below about 75 mbar, below about 50 mbar, or below about 25 mbar. For example, $CO_2$ concentration can be deemed "trace" when the partial pressure of $CO_2$ in a system is less than 50 mbar. An example of a system having a trace $CO_2$ concentration is a system having at least 95% $N_2$. As used herein, "confined spaces" refer to areas which have limited or no supply of fresh air. Examples of confined spaces include aeronautical vessels such as an airplane or space, submarines, and industrial vessels such as those with small hatched openings.

Metal organic frameworks (MOFs) are a versatile and promising class of crystalline solid state materials which allow porosity and functionality to be tailored towards various applications. For example, MOF materials exhibit exceptionally high specific surface area, in addition to tunable pore size and functionality (e.g., $CO_2$ selectivity, and $H_2O$ tolerance), which make them suitable for many applications including gas storage, gas separation, catalysis, drug delivery, light-emitting devices, and sensing.

Generally, MOFs comprise a network of nodes and ligands, wherein a node has a connectivity capability at three or more functional sites, and a ligand has a connectivity capability at two functional sites each of which connect to a node. Nodes are typically metal ions or metal containing clusters, and, in some instances, ligands with node connectivity capability at three or more functional sites can also be characterized as nodes. In some instances, ligands can include two functional sites capable of each connecting to a node, and optionally one or more additional functional sites which do not connect to nodes within a particular framework. In some embodiments, ligands can be poly-functional, or polytopic, and comprise two or more functional sites capable of each connecting to a node. In some embodiments, polytopic ligands can be heteropolytopic, wherein at least two of the two or more functional sites are different.

A MOF can comprise a metal-based node and an organic ligand which extrapolate to form a coordination network. Such coordination networks have advantageous crystalline and porous characteristics affecting structural integrity and interaction with foreign species (e.g., gases). The particular combination of nodes and ligands within a framework will dictate the framework topology and functionality. Through ligand modification or functionalization, the environment in the internal pores can be modified to suit specific applications.

A MOF can be represented by the formula [(node)a(ligand)b(solvent)c]n, wherein n represents the number of molecular building blocks. Solvent represents a guest molecule occupying pores within the MOF, for example as a result of MOF synthesis, and can be evacuated after synthesis to provide a MOF with unoccupied pores. Accordingly, the value of c can vary down to zero, without changing the definitional framework of the MOF. Therefore, in many instances, MOFs as provided herein can be defined as $[(node)_a(ligand)_b]_n$, without reference to a solvent or guest molecule component.

Figure 1B:
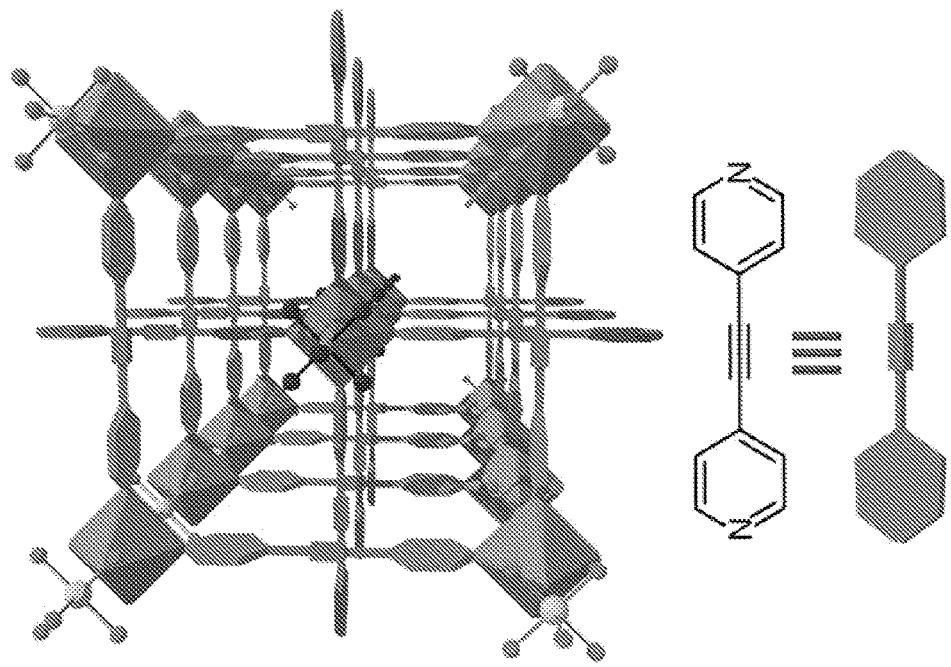
FIG. 1B illustrates a perspective view of a SIFSIX-n-M MOF coordinated by dipryidilacetylene ligands, according to one or more embodiments.

An example of a class of MOFs is SIFSIX-n-M, wherein n is at least two, and M can comprise Cu, Zn, Co, Mn, Mo, Cr, Fe, Ca, Ba, Cs, Pb, Pt, Pd, Ru, Rh, and Cd. The SIFSIX-n-M MOF class is isoreticular across its metal analogues (i.e., each M analogue has the same framework topology) and is characterized by periodically arrayed hexafluorosilicate (SIFSIX) octahedral pillars. SIFSIX-n-M MOFs have many desirable characteristics, including tunable pore sizes, which lend the various analogues well to a number of industrial applications. FIG. 1A-B show examples of SIFSIX-n-MOF analogues.

FIG. 1A illustrates a SIFSIX-n-M MOF coordinated by pyrazine ligands. Specific analogues of this MOF include SIFSIX-3-Cu and SIFSIX-3-Zn, among others. Such SIFSIX-3-M analogues are iso-structural, based on pyrazine/M (II) 2-D periodic $4^4$ square grids pillared by $(SiF_6)^{2-}$ anions. SIFSIX-3-Zn MOFs comprising pyrazine ligands can have average pore sizes of about 3.84 Å and BET apparent surface areas of about 250 $m^2 \cdot g^{-1}$ (determined from the $CO_2$ adsorption isotherm at 298K). SIFSIX-3-Cu MOFs comprising pyrazine ligands can have average pore sizes of about 3.50 Å (NLDFT) and BET and Langmuir apparent surface areas of ca. 300 $m^2 \cdot g^{-1}$ (determined from the $CO_2$ adsorption isotherm at 298K). FIG. 1B illustrates a SIFSIX-n-M MOF coordinated by dipryidilacetylene (DPA) ligands. A specific analogue of this MOF is SIFSIX-2-Cu-i, among others. SIFSIX-2-Cu—I MOFs comprising DPA ligands can have average pores size of 5.15 Å and BET apparent surface areas (determined by $N_2$ adsorption) of about 735 $m^2 \cdot g^{-1}$. In FIG. 1A-B, guest molecules have been omitted for clarity.

SIFSIX-n-M MOFs can be coordinated by a variety of organic ligands. In some embodiments, the ligand can be any bidentate (i.e., bi-functional) N-donor linkers based on monocyclic or polycyclic group (aromatic or not). In some embodiments, a ligand can comprise a polydentate, or poly-functional ligand, such as a bi-functional ligand, a tri-functional ligand, or ligands with four or more functional sites. In some embodiments, a ligand can comprise an N-donor linker. In some embodiments a ligand can comprise a poly-functional ligand. In some embodiments, a ligand can comprise a plurality of N-donor functional groups. Pyrazine is an example of a ligand with two N-donor functional groups. In some embodiments, a ligand can comprise a monocyclic or polycyclic group structure, wherein the cyclic groups can be aromatic or nonaromatic. In some embodiments, a ligand can comprise a nitrogen-containing monocyclic or polycyclic group structure. In some embodiments, a ligand can comprise a nitrogen-containing heterocyclic ligand, including pyridine, 4,4'-Bipyridin, pyrazine, pyrimidine, pyridazine, triazine, thiazole, oxazole, pyrrole, imidazole, pyrazole, triazole, oxadiazole, thiadiazole, quinoline, benzoxazole, benzimidazole, 1,4-Diazabicyclo[2.2.2]octane (DABCO), 1,2-bis(4-pyridyl)acetylene (dpa), and tautomers thereof.

The SIFSIX-n-M MOFs presented herein provide uniformly distributed and non-reactive $CO_2$ adsorption energetics and remarkable $CO_2$ adsorption properties, uptake and selectivity in highly diluted gas streams. Such performance is currently unachievable with other class of porous materials. In particular, SIFSIX-n-M MOFs are suitable for trace $CO_2$ removal applications, due to their strong $CO_2$ adsorption sites. SIFSIX MOF materials exhibit very high (non-reactive) $CO_2$ energetics, but fully reversible physical driven adsorption-desorption operations at very mild conditions. The ideal combination of contracted pore size and the high charge density also provide unprecedented $CO_2$ uptake and selectivity over $H_2$, $CH_4$ and $N_2$ at very low partial pressures.

SIFSIX-n-M MOFs are suitable for post-combustion capture (at $CO_2$ partial pressures of about 100 mbar), but also excellent features suitable for natural and biogas upgrading as well as pre-combustion capture (high $CO_2$ concentration and high pressure).

Figure 1C:
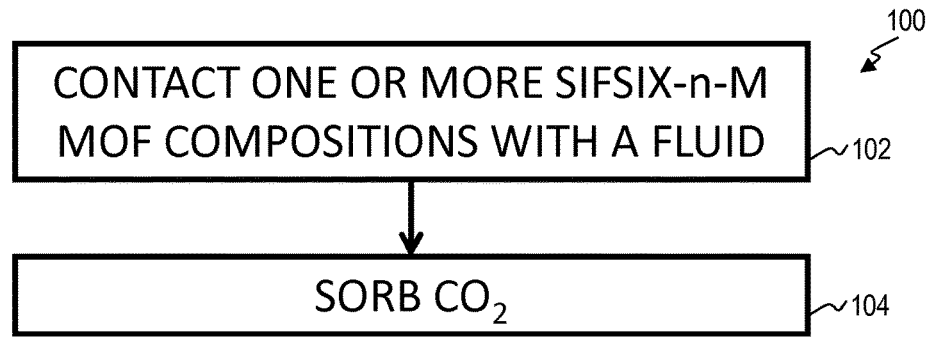
FIG. 1C-D illustrate block flow diagrams of a methods for removing $CO_2$ from a fluid, according to one or more embodiments.

FIG. 1C illustrates a block flow diagram of a method 100 for removing $CO_2$ from a fluid via a SIFSIX-n-M MOF. Method 100 includes contacting 102 one or more SIFSIX-n-M MOF compositions with a fluid and sorbing 104 $CO_2$ from the fluid with the one or more SIFSIX-n-M MOF compositions. In particular, method 100 can include contacting 102 one or more SIFSIX-n-Cu and SIFSIX-n-Zn MOF compositions with a fluid and sorbing 104 $CO_2$ from the fluid with the one or more SIFSIX-n-Cu and SIFSIX-n-Zn MOF compositions. In particular, method 100 can include contacting 102 one or more SIFSIX-n-M MOF compositions with a fluid and sorbing 104 $CO_2$ from the fluid with the one or more SIFSIX-n-M MOF compositions, wherein M can comprise Cu, Zn, Co, Mn, Mo, Cr, Fe, Ca, Ba, Cs, Pb, Pt, Pd, Ru, Rh, and Cd. SIFSIX-n-M MOFs can comprise bidentate organic ligands. SIFSIX-n-M MOFs can comprise bidentate N-donor organic ligands. The bidentate N-donor organic ligands can comprise a cyclic moiety. The bidentate N-donor organic ligands can include monocyclic or polycyclic moieties. Monocyclic and polycyclic bidentate N-donor organic ligands can be aromatic and non-aromatic. SIFSIX-n-M MOFs can comprise pyrazine or DPA ligands.

Contacting 102 can include mixing, bringing in close proximity, chemically contacting, physically contacting or combinations thereof. Fluids can include general liquids and gases which include $CO_2$. In particular, fluids can include general liquids and gases which include trace amounts of $CO_2$. In some embodiments, fluids include industrial process fluids. In some embodiments, fluids include breathing air. Breathing can include any air which is inhaled by a living organism. Breathing air can include air in a confined space. Breathing air can include air provided by a breathing device such as a medical device and a SCUBA tank. Fluids can include one or more of water, $N_2$, $O_2$, and $H_2$. In a specific embodiment, fluids can include $CO_2$ and one or more of water, $N_2$, $O_2$, and $H_2$.

In one embodiment, sorbing 104 comprises absorbing. In one embodiment, sorbing 104 comprises adsorbing. In one embodiment, sorbing 104 comprises a combination of adsorbing and absorbing. Sorbing 104 can include selective sorption of $CO_2$ over other species present within the fluid. For example, sorbing 104 can include selectively sorbing $CO_2$ over one or more of water, $N_2$, $O_2$, and $H_2$. The SIFSIX-n-M MOF compositions can sorb about 1% to about 99.9%, about 1% to about 90%, about 1% to about 50% or about 1% to about 30% of one or more compounds in a fluid. Sorbing 104 can include reducing the $CO_2$ concentration in a fluid to less than about 1%, less than about 0.5%, less than about 0.1%, or less than about 0.01%.

Sorbing 104 can occur at ambient temperature, at an elevated temperature, at a cooled temperature, or over a temperature range. In one embodiment, a temperature can be selectively changed to manipulate sorption and/or desorption of different compounds. Sorbing 104 can occur at ambient pressure, at an elevated pressure, at a cooled pressure, or over a pressure range. In one embodiment, pressure can be selectively changed to manipulate sorption and/or desorption of different compounds. In addition to or in the alternative to, a concentration of one or more SIFSIX-n-M MOF compositions can be varied to affect a rate and/or magnitude of sorbing 104. One or more of temperature, pressure and SIFSIX-n-M MOF concentration can be regulated to produce a simultaneous sorption of compounds, or a subsequent, step-wise sorption (i.e., in series) of compounds from a fluid. In series sorption generally includes sorbing a quantity of a first compound via a MOF, and subsequently sorbing a quantity of a second compound via the same MOF while at least a portion of the quantity of the first compound remains sorbed. Simultaneous sorption generally includes contacting a plurality of compounds with an MOF, and sorbing a quantity of each of the two compounds with the MOF.

Figure 1D:
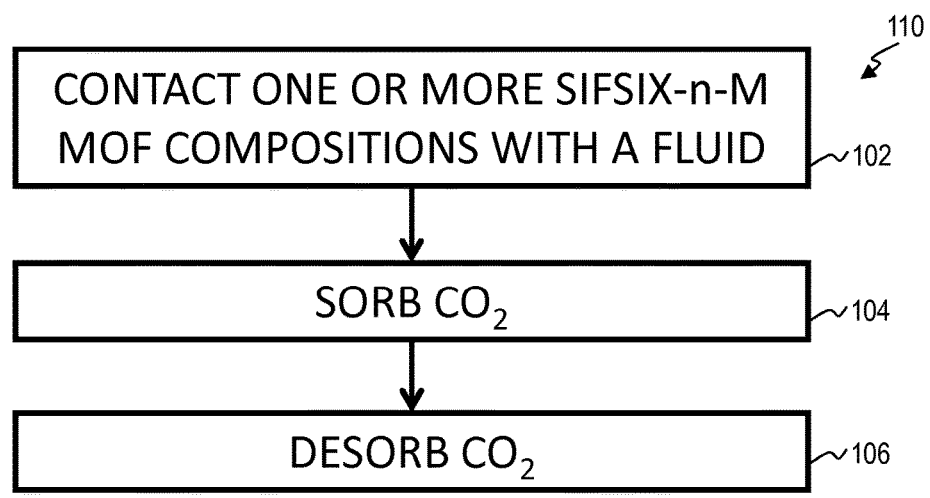

Sorbing 104 can be reversible. FIG. 1D illustrates a block flow diagram of a method 110 for removing $CO_2$ from a fluid via a SIFSIX-n-M MOF. Method 110 includes contacting 102 one or more SIFSIX-n-M MOF compositions with a fluid, sorbing 104 $CO_2$ from the fluid with the one or more SIFSIX-n-M MOF compositions, and desorbing 106 $CO_2$ from the one or more SIFSIX-n-M MOF compositions. Method 110 can constitute one sorbing cycle. SIFSIX-n-M MOFs can perform a plurality of sorbing cycles and maintain structural integrity. Optimal $CO_2$ energetics of SIFSIX-n-M MOF compositions which are strong, uniform, and relatively low enable reversible sorption.

Methods 100 and 110 can be utilized in the context of breathing systems. Specifically, sorbing 104 can be utilized within a breathing system. Efficient removal of $CO_2$ at low concentrations is vital for the proper operation of breathing systems in confined spaces such as submarines and aerospace shuttles. During long-term space flight and submarine missions, $CO_2$ must be removed from the air and recycled because resupply opportunities are scarce. An average crew member requires approximately 0.84 kg of oxygen and emits approximately 1 kg of carbon dioxide. Thus, the ability to continuously purify the exhaled air (with a maximum $CO_2$ concentration of 2-5%) will lead to an optimal recycling and considerable reduction in fresh air supply in remote confined spaces. The problem of the existing technologies is the capture capacity/day which is low due to mainly to the long temperature swing adsorption cycling mode (TSAM). The TSAM is mainly determined by the way the adsorbent is cleaned. In the case of low $CO_2$ concentration removal, chemical (amine supported) adsorbents are preferred with a Heat of adsorption of 70-100 kJ/mol, —a parameter indicative of the energy required to clean the material after each adsorption cycle. Implementing MOF-based physical adsorption (such as SIFISIX-Cu-3) in a process such as VTSA or VSA (with mild vacuum) will increase the $CO_2$ removal capacity/day and decrease the energy penalty needed for regeneration.

Methods 100 and 110 can be utilized in the context of anaesthesia. Specifically, sorbing 104 can be utilized within an anesthetic system. The use of anaesthesia machines is a growing clinical trend worldwide, driven by the need to reduce costs and improve patient care via the use of efficient $CO_2$ sorbents. $CO_2$ removal features in anaesthesia machines are particularly important in semi-closed or closed rebreathing systems, as the rebreathing fraction is at least 50% of the exhaled gas volume. Exhaled gas volume is directed back to the patient after proper $CO_2$ removal. Sodalime is currently the sorbent of choice in most commercially available anaesthesia machines. This sorbent exhibits a high $CO_2$ removal efficiency from exhaled air, with an average continuous operation of about 24 hours using a pre-packed commercial cartridge. Nevertheless, a major drawback of this technology is that one sodalime cartridge can only be used for a single cycle and is non-recyclable, generating therefore undesirable waste that should be disposed properly.

In case of anaesthesia machines, the use of recyclable SIFSIX-n-M MOFs allow the same regeneratable cartridge much longer durations than 24 hours. A single SIFSIX-n-M MOF cartridge can be in operation while two of the same are in regeneration, for example. Assuming the $CO_2$ uptake of MOF is 10 times lower than sodalime but its life time is 10000 higher than the commercial adsorbents, this can lead to an increase in the overall capacity by 1000 times. SIFSIX-n-M MOF cartridges can be replace existing cartridges, such as sodalime cartridges, to without any major changes in the existing anaesthesia machines. The main change in case of the recyclable MOF can be the addition of small devices (desorber) for re-activation of the MOF cartridges or in-situ continuous temperature-pressure adsorption system.

Methods 100 and 110 can be utilized in the context of alkaline fuel cells (AFCs). Specifically, sorbing 104 can be utilized within an AFC. AFCs require a $CO_2$-free feedstock of oxygen and hydrogenfuel, as even trace amounts of $CO_2$ (i.e. 300 ppm) can degrade AFC electrolytes through progressive carbonation. During typical AFC operation, air is transmitted through the gas diffusion layer of the cathode to the catalyst layer which can include a KOH solution. Any $CO_2$ present in the air can react with the KOH to form $K_2CO_3$ in the catalyst layer, thereby reducing fuel oxidation and oxygen reduction kinetics and AFC power output, inducing precipitation of carbonate salts in porous AFC electrodes, and reducing AFC electrolyte conductivity. SIFSIX-n-M MOFs can capably remove trace amounts of $CO_2$ from any air contacting AFC catalyst layers. The ability of SIFSIX-n-M MOFs to regenerate (i.e., desorb $CO_2$ while retaining structural integrity) after $CO_2$ sorption lends further benefits to fuel cell applications such as military vehicles, which can lack access to fresh $CO_2$ sorbents while in combat.

Example 1: Synthesis of SIFSIX-3-Cu MOF

A methanol solution (5.0 mL) of pyrazine (pyz, 0.30 g, 3.0 mmol) was layered in a glass tube onto a methanol solution (5.0 mL) of $CuSiF_6 \cdot xH_2O$ (0.325 g, 0.6 mmol). Upon layering, a fast formation of light violet powder was observed, and the powder was left for 24 hours in the mother solution. The SIFSIX-3-Cu powder was then collected and washed extensively with methanol then dried under vacuum. The thermal gravimetric analysis (TGA) of the SIFSIX-3-Cu showed a weight loss of about 10% for the dried sample in the range of 50-150° C. attributed to guest molecules. From PXRD measurements, the cell parameters, a=b=6.919(1) Å, c=7.906(1) Å, were refined by a whole powder pattern fit using the Le Bail method, implemented in FULLPROF software. The final Rietveld refinement yielded: $R_{Bragg}$=0.051 and $R_{Factor}$=0.056.

Figure 2A:
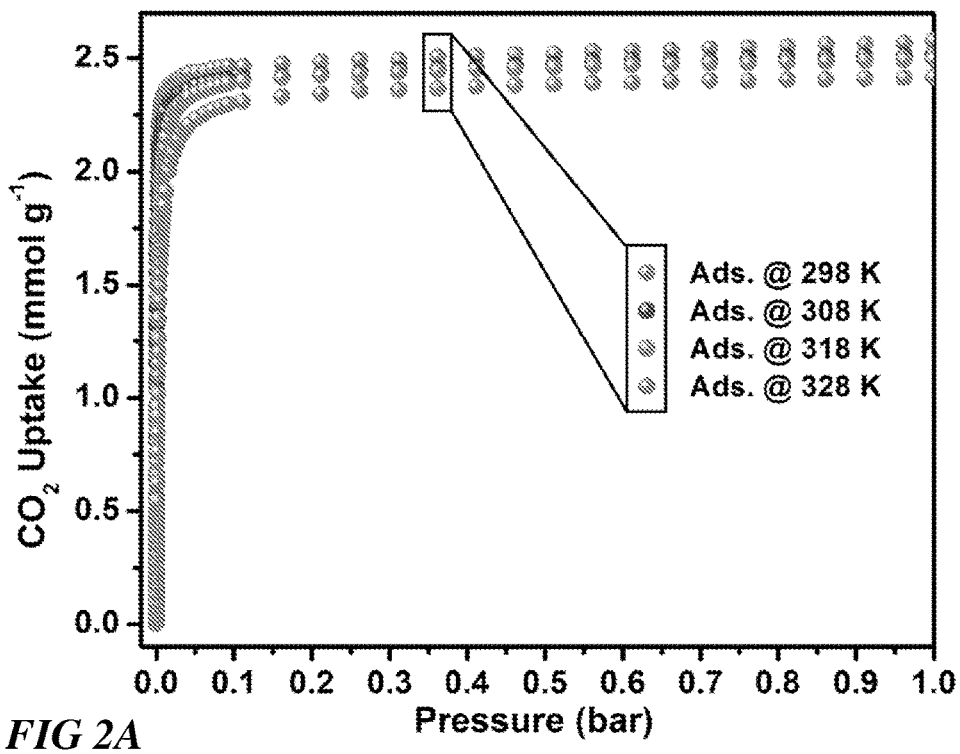
FIG. 2A illustrates $CO_2$ adsorption isotherms at variable temperatures for a SIFSIX-3-Cu MOF, according to one or more embodiments.

FIG. 2A illustrates $CO_2$ adsorption isotherms at variable temperatures for the SIFSIX-3-Cu MOF. The Cu analogue shows the same promising adsorption properties as SIFSIX-3-Zn analogues. Moreover, the Cu analogue shows even steeper variable temperature adsorption isotherms at very low pressures, indicative of relatively stronger $CO_2$— SIFSIX-3-Cu interactions. These results emphasize the potential of SIFSIX-3-Cu for $CO_2$ capture applications.

Figure 2B:
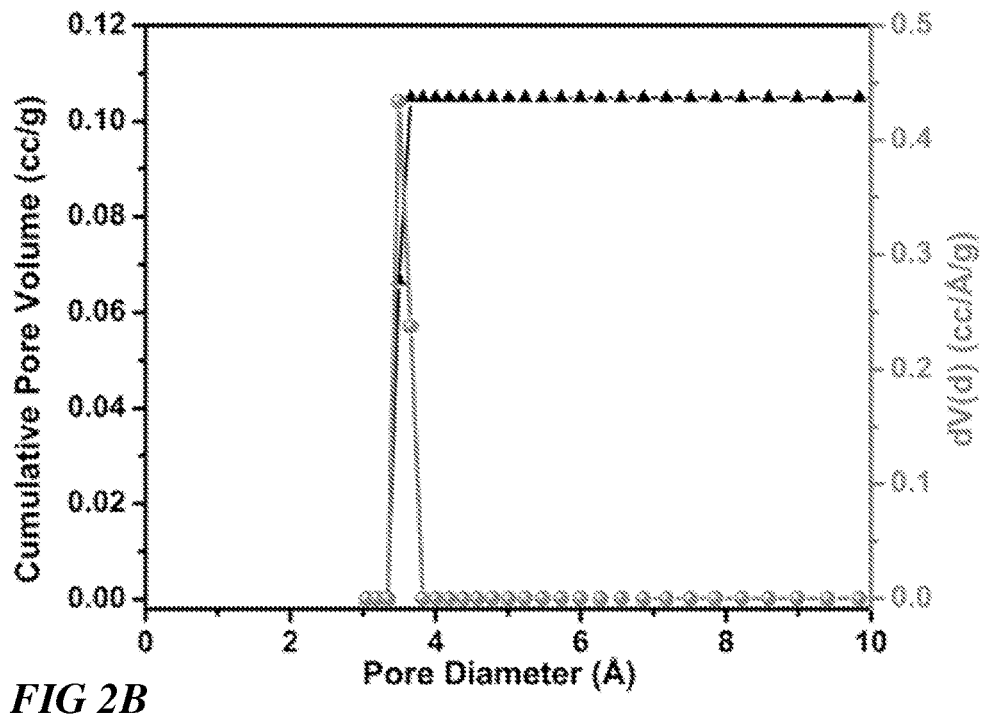
FIG. 2B illustrates a pore size distribution for a SIFSIX-3-Cu MOF, according to one or more embodiments.

The SIFSIX-3-Cu MOF exhibited a slightly smaller unit cell as compared to its Zn analogue (378 vs. 388 Å$^3$). The attributed to the relatively stronger bonding between the Cu(II) and the pyrazine. FIG. 2B illustrates a pore size distribution for the SIFSIX-3-Cu MOF, as determined from the $CO_2$ adsorption isotherms, using a $CO_2$ at 273 K NLDFT model. The relatively sharp pore size distribution (PSD) analysis centred at 3.5 Å yields a smaller average pore size than the SIFSIX-3-Zn analogue average pore size of 3.84 Å, which is in good agreement with the determined unit cell sizes. These determinations are supported by a rational based on conventional coordination chemistry which suggests that replacement of Zn(II) by Cu(II) to form an iso-structural SIFSIX-3-Cu will potentially induce an additional pore contraction due to Jahn-Teller distortions of the octahedral coordination geometry of Cu(II), $CuN_4F_2$. The Cu(II) has an open shell valence electron configuration $3d^9$, in contrast to Zn(II) with a close shell $3d^{10}$, and thus will experience a distorted octahedral coordination geometry with potentially elongated Cu—F (fluorine) bonds and relatively shorter Cu—N (nitrogen) bonds.

Example 2: $CO_2$ Sorption by Various MOFs

Figure 3A:
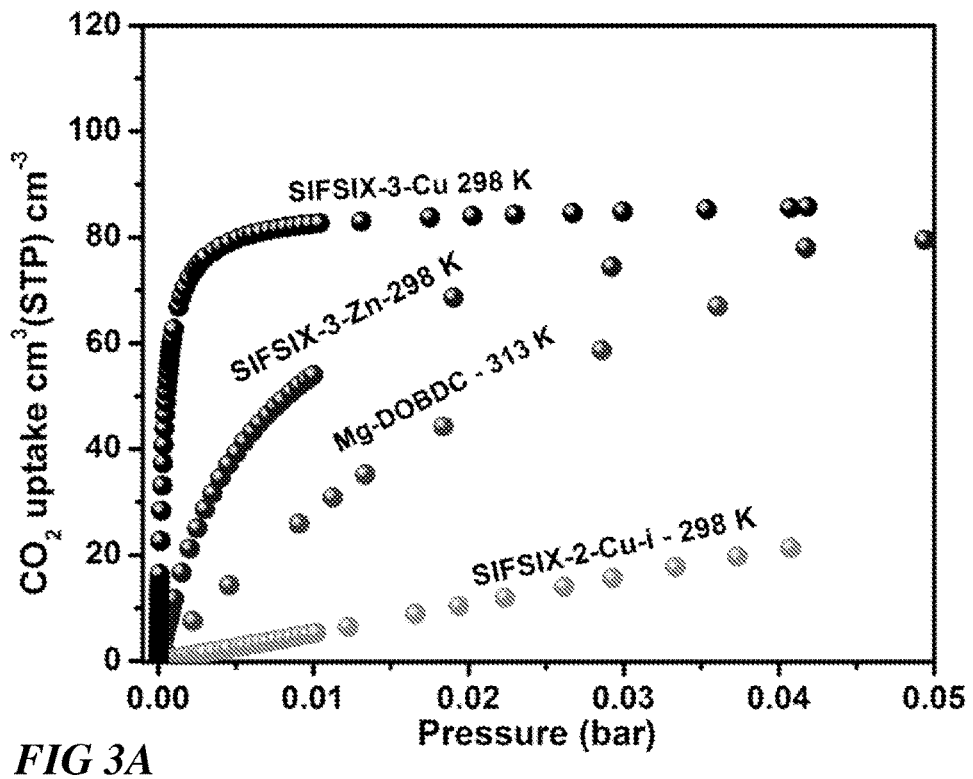
FIG. 3A illustrates $CO_2$ volumetric uptake for various SIFSIX metal organic frameworks, according to one or more embodiments.
Figure 3B:
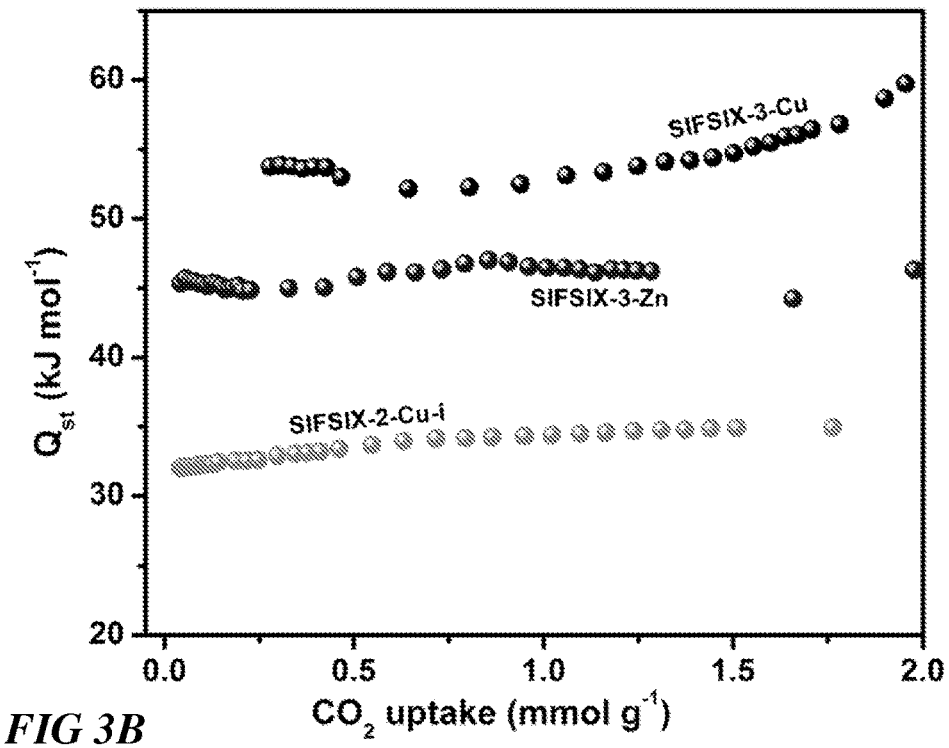
FIG. 3B illustrates isosteric heats of adsorption at low coverage for SIFSIX-3-Cu, SIFSIX-3-Zn and SIFSIX-2-Cu—I metal organic frameworks, according to one or more embodiments.

FIG. 3A illustrates $CO_2$ volumetric uptake for SIFSIX-3-Cu t 298 K compared to SIFSIX-3-Zn, SIFSIX-2-Cu—I and Mg-MOF-74. FIG. 3B illustrates isosteric heats of adsorption at low coverage for SIFSIX-3-Cu, SIFSIX-3-Zn and SIFSIX-2-Cu—I. Upon the substitution of Zn by Cu, the $Q_{st}$ of $CO_2$ adsorption in the contracted structure increased by 20%, from 45 to 54 kJ mol$^{-1}$ (FIG. 3b), in perfect agreement with the relatively steeper $CO_2$ adsorption isotherms in the case of the Cu analogue at very low pressure. This increase is mainly attributed to the small unit cell and the contracted pore size of the Cu analogue which in turn tend to increase the electron density surrounding the adsorbed $CO_2$ molecules. The $Q_{st}$ of $CO_2$ adsorption is an intrinsic property that dictates the affinity of the pore surface toward $CO_2$, which in turn plays a major role in determining the adsorption selectivity and the necessary energy to release $CO_2$ during the regeneration step.

Although the $Q_{st}$ for $CO_2$ was slightly above the typical range of fully reversible $CO_2$ adsorption (30-50 kJ mol$^{-1}$),[22] SIFSIX-3-Cu was fully and quickly evacuated at 323 K in vacuum (or under $N_2$ flow environment). As in case of SIFSIX-3-Zn and SIFSIX-2-Cu-i, the $Q_{st}$ for $CO_2$ adsorption was mostly constant up to relatively high $CO_2$ loadings indicating homogenous binding sites over the full range of $CO_2$ loading. The further increase of $CO_2$ Qst for SIFSIX-3-Cu at the average loading of 1.5 mmol·g$^{-1}$ can be explained by the spark of the $CO_2$—$CO_2$ interactions or possible experimental errors close to the saturation (plateau) of adsorption isotherm.

Example 3A: Trace $CO_2$ Uptake of Various MOFs

The steep $CO_2$ adsorption isotherms over a wide range of temperatures exhibited by SIFSIX-n-M MOFs suggest potential for the same for trace $CO_2$ adsorption applications (e.g., diluted streams in vacuum or in mixtures containing a large fraction of $N_2$ up to 95%). In order to highlight the concealed potential of these MOFs for low $CO_2$ concentration applications (i.e. involving $CO_2$ concentration below 5%, below 50 mbar $CO_2$ partial pressure, such as anaesthesia machines and pre-purification before air separation and air capture), single gas $CO_2$ adsorption properties were evaluated for SIFSIX-2-Cu-i and SIFSIX-3-Zn. Table 1 summarizes the $CO_2$ adsorption uptake at variable low $CO_2$ concentration (partial pressures) for SIFSIX compounds as compared to Mg-MOF-74 and amine supported materials (including MOFs), relevant to different traces $CO_2$ removal applications. The SIFSIX-3-Cu MOF also showed even higher $CO_2$ uptake at 400 ppm and 328 K than the corresponding uptake at 323 K for amine functionalized Mg-dobpdc-mmen (data not included).

TABLE 1

$CO_2$ adsorption uptake at various traces $CO_2$ concentration and at 298 K in comparison to the most promising MOFs and other various amine supported materials.

| Adsorbent | uptake at 400 ppm (0.4 mbar) | Uptake at 5000 ppm (5 mbar) | Uptake at 10000 ppm (10 mbar) | $CO_2$ Qst (kJ · mol$^{-1}$) |
|---|---|---|---|---|
| SIFSIX-2-Cu-i | 0.0684[c]/0.2[d] | 0.097[c]/2.7[d] | 0.19[c]/5.32[a] | 32 |
| SIFSIX-3-Zn | 0.13[c]/5.6[d] | 1.12[c]/39.26[d] | 1.53[c]/53.97[d] | 45 |
| SIFSIX-3-Cu | 1.24[c]/43.9[d] | 2.26[c]/79.8[d] | 2.34[c]/82.5[d] | 54 |
| — | — | — | — | 47 |
| Mg-MOF-74 | 0.088[c]/1.8[d] | 0.7[c]/14.3[d] | 1.27[c]/25.86[d] | ND |
| Mg-MOF-74-ED[a,g] | 1.5[c] | ND | ND | 70 |
| Mg-dobpdc-mmen[b,g] | 2[c] | 2.5[c] | 2.75[c] | 92 |
| TRI-PE-MCM-41[f,g] | 1[c] | 1.45[c] | 1.6[c] | ND |
| HAS[f,g] | 1.7[c] | ND | ND | |

[a]Ethylenediamine functionalized;
[b]N,N-dimethylethylenediamine functionalized;
[c]mmol · g$^{-1}$;
[d]cm$^3$ (STP)/cm$^3$;
[e] at 328 K;
[f]Amine supported silica;
ND: non determined.
[g]Chemical adsorbent The contraction of the pore size from 5.15 Å (for SIFSIX-2-Cu-i) to 3.8 Å (for SIFSIX-3-Zn) has prompted a drastic increase in $CO_2$ uptake and consequently a recorded highest $CO_2$ uptake ever reported for a given MOF in the range under 5% $CO_2$. Specifically, SIFSIX-3-Zn showed an order of magnitude higher volumetric $CO_2$ uptake (55 cm$^3$ (STP)/cm$^3$) than other materials such as Mg-MOF-74, (28 cm$^3$ (STP)/cm$^3$) at 10 mbar (1% $CO_2$), while UTSA-16, exhibits much lower $CO_2$ uptake similar to SIFSIX-2-Cu-i.

In the context low concentration applications (400 ppm-5%), the exhibits steep adsorption isotherms at very low $CO_2$ concentration of the SIFSIX-3-Cu analogue, as shown in FIG. 3A, translate into the highest uptake ever reported for MOFs without unsaturated metal centers (UMCs) or exposed amino functionality at low $CO_2$ pressures below 38 torr (0.05 bar). This can be even more appealing owing to its fully physical adsorption nature where complete and fast desorption of $CO_2$ was established under vacuum at only 323 K. At 7.6 torr (0.01 bar) SIFSIX-3-Cu uptakes 82.6 cm$^3$(STP)·cm$^{-3}$ vs. 55 and 28 cm$^3$(STP)·cm$^{-3}$ for SIFSIX-3-Zn and Mg-MOF-74, respectively. The gravimetric uptake of SIFSIX-3-Cu at 400 ppm and 298 K (1.24 mmol·g$^{-1}$) is ca. 10 and 15 times higher than the corresponding uptakes for SIFSIX-3-Zn (0.13 mmol·g$^{-1}$) and Mg-MOF-74 (0.08 mmol·g$^{-1}$) and even higher than the observed uptakes for most amine-supported silica materials (with optimal compromise of amine loading and kinetics) at 298 K (for example TRI-PE-MCM-4 (1 mmol·g$^{-1}$)[10,22]).

Example 3B: Column Breakthrough Tests of SIFSIX MOFs

Figure 4A:
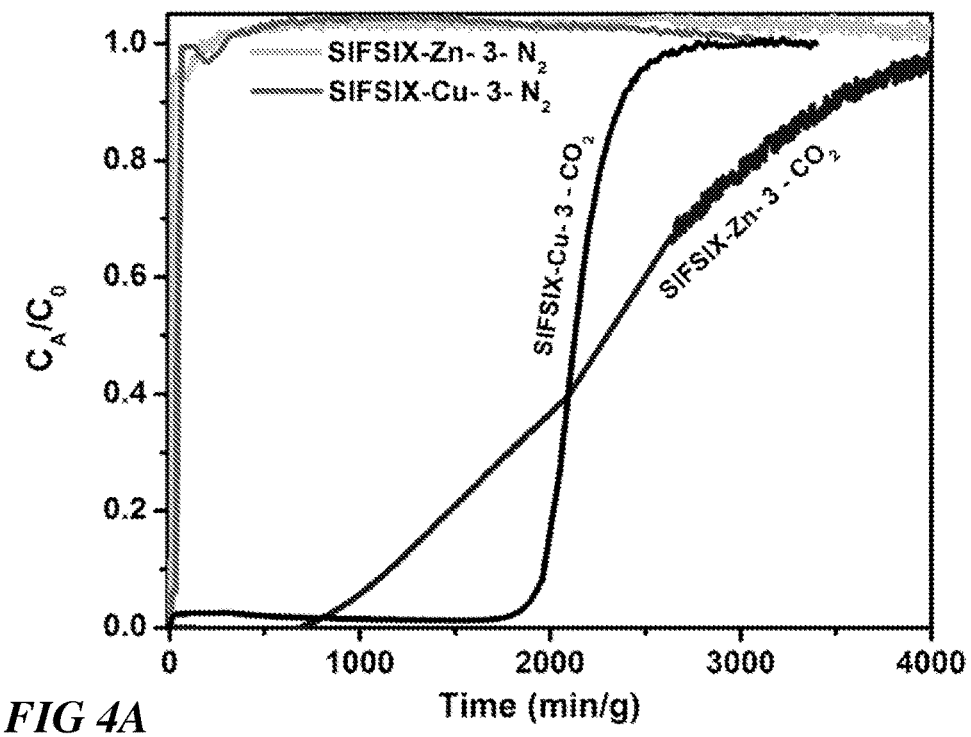
FIG. 4A illustrates a column breakthrough test of $CO_2$/$N_2$:1000 ppm/99.9% for SIFSIX-3-Cu and SIFSIX-3-Zn metal organic frameworks in dry conditions, according to one or more embodiments.
Figure 4B:
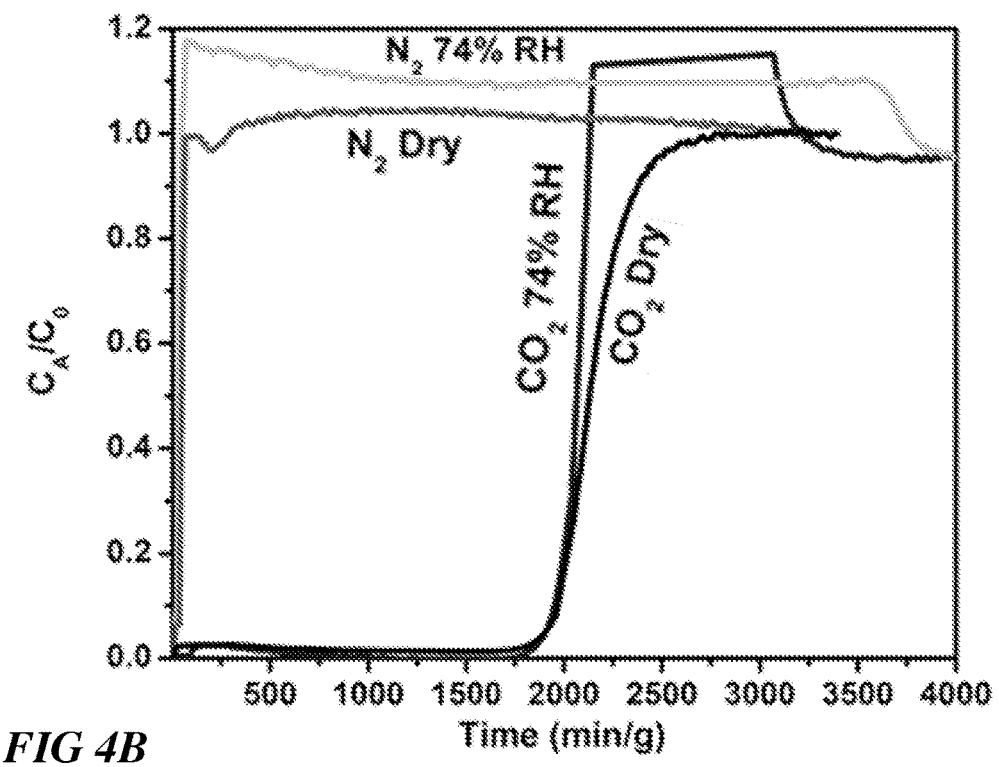
FIG. 4B illustrates a column breakthrough test of $CO_2$/$N_2$:1000 ppm/99.9% for a SIFSIX-3-Cu metal organic framework in dry conditions as well as at 74% relative humidity (RH), according to one or more embodiments.

The $CO_2$ selectivity exhibited by SIFSIX-3-Zn and SIFSIX-3-Cu MOFs was investigated experimentally at trace $CO_2$ concentrations using column breakthrough tests for binary $CO_2/N_2$:1000 ppm/99.9% mixtures at 298 K in dry conditions, as well as in humid conditions. FIG. 4A illustrates a column breakthrough test of $CO_2/N_2$:1000 ppm/99.9% for SIFSIX-3-Cu and SIFSIX-3-Zn MOFs in dry conditions. FIG. 4B illustrates a column breakthrough test of $CO_2/N_2$:1000 ppm/99.9% for SIFSIX-3-Cu in dry conditions as well as at 74% relative humidity (RH). In dry conditions, the first $CO_2$ signal downstream the column was observed only after ca. 798 and ca. 1922 min·g$^{-1}$ for SIFSIX-3-Zn and SIFSIX-3-Cu, respectively after starting continuous $CO_2/N_2$ gas mixture flux (5 cm$^3$·min$^{-1}$), while $N_2$ breakthrough occurred immediately within a few seconds. Accordingly, at 1000 ppm $CO_2$ and breakthrough time, SIFSIX-3-Cu shows higher selectivity (ca. 10500) than SIFSIX-3-Zn (7259). It should be noted that calculated and measured selectivity exceeding 1000-2000 are often subject to uncertainties associated with measurement of the gas uptake of weakly adsorbed gases ($N_2$) in the mixture, thus the reported selectivity is highly qualitative and aimed mainly for relative comparison of the studied compounds in this work. The steeper $CO_2$ signal after breakthrough for SIFSIX-3-Cu as compared to the Zn analogue is a direct indication of the steeper $CO_2$ adsorption for the Cu analogue as shown in FIG. 3A.

The $CO_2$ removal selectivity at 1000 ppm $CO_2$ for SIFSIX-3-Cu MOFs was not affected by the presence of humidity as shown from the column breakthrough tests performed on both compounds at the relative humidity (RH) of 74%. This unprecedented finding was also valid in case of SIFSIX-3-Zn for the removal of low and higher $CO_2$ concentration. Finally, as was demonstrated for SIFSIX-3-Zn, SIFSIX-3-Cu is a recyclable and moisture stable MOFs.

Example 4: $CO_2$ Uptake Kinetic Study for SIFSIX-3-Cu MOFs

Kinetic studies of $CO_2$ and $CO_2/N_2$:10/90 adsorption on SIFSIX-3-Cu were carried out using the Rubotherm gravimetric apparatus operating in dynamic regime. Initially, the SIFSIX-3-Cu MOF was properly evacuated at 323 K in vacuum. In order to achieve an immediate constancy of pressure (0.5 bar) during kinetics tests and avoid the often noisy uptake during the rapid introduction of the studied gas, an initial baseline was set-up using helium gas at 0.5 bar for single gases and 1 bar for mixture, then the studied single gas or mixture is flushed with a flow of 300 ml/min to avoid any dependence of the kinetics on the mass flow controller.

The mechanistic behind the unprecedented selective $CO_2$ adsorption involving the unique synergetic effect of thermodynamics and kinetics was confirmed by the competitive kinetics of $CO_2/N_2$:10/90 gas mixture adsorption. As anticipated, the uptake at equal times for variable $CO_2$ compositions mixtures follows the behaviour of pure $CO_2$. Further, the total uptake of the $CO_2$ containing gas mixtures at equilibrium overlay perfectly with the equilibrium uptake for pure $CO_2$. These findings show that similarly to SIFSIX-3-Zn, when $CO_2$ containing mixtures are in contact with SIFSIX-3-Cu, $CO_2$ adsorbs stronger and faster than $N_2$, and, by analogy, also $O_2$, $CH_4$ and $H_2$. Adsorbed $CO_2$ thus occupies all available physical space and adsorption sites and subsequently exclude other gases, a desirable feature in many $CO_2$ separation and purification applications.

Example 5: Devices for $CO_2$ Removal

Figure 5:
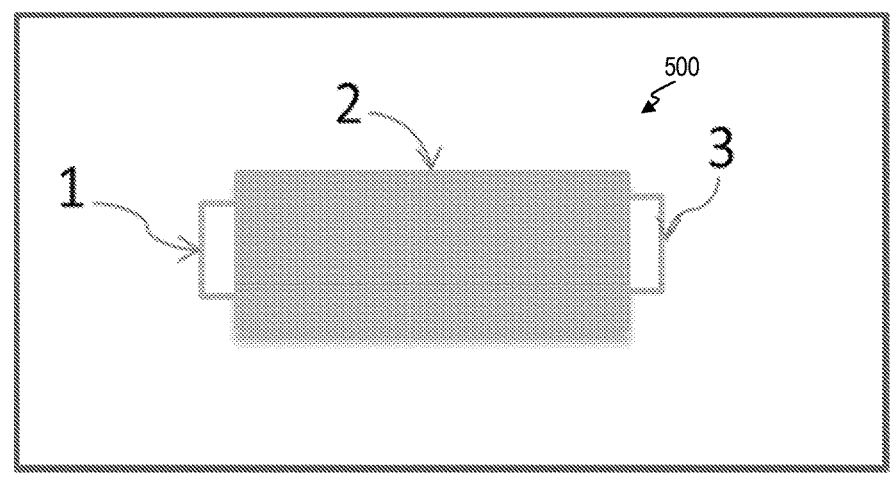
FIG. 5 illustrates a schematic view of a device for removing $CO_2$ from a gas, according to one or more embodiments.

FIG. 5 illustrates a schematic view of a device 500 for removing $CO_2$ from a gas, comprising a gas flow inlet 1, a housing for containing one or more SIFSIX-n-M MOF compositions 2 for sorbing $CO_2$, and a gas flow outlet 3. Sorbing can comprise absorbing, adsorbing, or a combination of absorbing and adsorbing. Gas can pass through gas flow inlet 1 and out gas flow outlet 3. Gas can include a mixture of gases having a $CO_2$ concentration of less than 5%.

What is claimed is:

1. A method of removing $CO_2$ from a fluid, the method comprising:
   contacting a SIFSIX-3-Cu metal-organic framework with a fluid;
   sorbing $CO_2$ from the fluid with the SIFSIX-3-Cu metal-organic framework; and desorbing $CO_2$ from the SIFSIX-3-Cu metal-organic framework.

2. A method of removing $CO_2$ from a fluid, the method comprising:
   contacting a SIFSIX-3-Cu metal-organic framework with a fluid; and
   sorbing $CO_2$ from the fluid.

3. The method of claim 2, wherein the method further comprises desorbing $CO_2$.

4. The method of claim 2, wherein the concentration of $CO_2$ in the fluid is less than 10%.

5. The method of claim 2, wherein sorbing comprises reducing the $CO_2$ concentration in the fluid to less than about 1%.

6. The method of claim 2, wherein sorbing occurs in a confined space.

7. The method of claim 2, wherein the fluid is breathing air.

8. The method of claim 2, wherein the $CO_2$ in the fluid has a partial pressure less than 100 mbar.

9. The method of claim 2, wherein the fluid further comprises one or more of water, $N_2$, $O_2$, and $H_2$.

10. The method of claim 9, wherein sorbing $CO_2$ occurs selectively over one or more of water, $N_2$, $O_2$, and $H_2$.

11. The method of claim 10, wherein sorbing $CO_2$ occurs in the presence of humidity and selectivity for $CO_2$ is not affected.

12. The method of claim 2, further comprising one or more SIFSIX-n-M compositions, wherein n is at least 2 and M is a metal.

13. The method of claim 12, wherein the metal comprises Cu, Zn, Co, Mn, Mo, Cr, Fe, Ca, Ba, Cs, Pb, Pt, Pd, Ru, Rh, or Cd.

14. The method of claim 12, wherein n is 3.

15. The method of claim 12, wherein at least one of the one or more SIFSIX-n-M compositions comprise bidentate organic ligands.

16. The method of claim 12, wherein at least one of the one or more SIFSIX-n-M compositions comprise pyrazine or dipryidilacetylene ligands.

17. The method of claim 12, wherein at least one of the one or more SIFSIX-n-M compositions comprise a SIFSIX-3-Zn metal organic framework.

18. The method of claim 12, wherein one or more of the SIFSIX-3-Cu metal-organic framework and one or more SIFSIX-n-M compositions are included in a regeneratable cartridge of an anesthetic system or in a catalyst layer of an alkaline fuel cell, wherein the sorbing occurs in the anesthetic system or the alkaline fuel cell, respectively.

19. The method of claim 12, wherein at least one of the one or more SIFSIX-n-M compositions comprise bidentate N-donor organic ligands.

20. The method of claim 19, wherein the bidentate N-donor organic ligands each comprise a cyclic moiety.

* * * * *